United States Patent
Whitton et al.

(10) Patent No.: US 10,548,506 B2
(45) Date of Patent: *Feb. 4, 2020

(54) MAGNETIC RESONANCE VISIBLE ASSEMBLY FOR ENCODING INFORMATION

(71) Applicant: SYNAPTIVE MEDICAL (BARBADOS) INC., Bridgetown (BB)

(72) Inventors: Gregory A. Whitton, Toronto (CA); Timotheus Gmeiner, Toronto (CA); Fergal Kerins, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/294,182

(22) Filed: Oct. 14, 2016

(65) Prior Publication Data

US 2017/0035527 A1    Feb. 9, 2017

Related U.S. Application Data

(63) Continuation-in-part of application No. PCT/IB2015/053396, filed on May 8, 2015.

(51) Int. Cl.
*A61B 5/055* (2006.01)
*A61B 90/00* (2016.01)
(Continued)

(52) U.S. Cl.
CPC ............. *A61B 5/055* (2013.01); *A61B 90/39* (2016.02); *A61B 90/96* (2016.02); *G01R 33/58* (2013.01);
(Continued)

(58) Field of Classification Search
None
See application file for complete search history.

(56) References Cited

U.S. PATENT DOCUMENTS 6,333,970 B1   12/2001  LeMaitre et al.
2004/0167391 A1*  8/2004  Solar ............... A61B 90/39
                                                                                600/411
(Continued)

FOREIGN PATENT DOCUMENTS

WO    2014032171 A1    3/2014

OTHER PUBLICATIONS

PCT International Search Report and Written Opinion, PCT/IB2015/053396, dated Aug. 12, 2015.
(Continued)

*Primary Examiner* — Bill Thomson
*Assistant Examiner* — Farouk A Bruce
(74) *Attorney, Agent, or Firm* — Quarles & Brady LLP; Jonathan Stone

(57) ABSTRACT

Systems and methods for manufacturing and using magnetic resonance ("MR") visible labels, markers, or assemblies to encode information unique to the subject or object being imaged by a magnetic resonance imaging ("MRI") system are provided. The use of such MR-visible labels, markers, or assemblies enables unique information associated with the subject or object being imaged to be encoded into the images of the subject or object. This information can be used to anonymize protected health information ("PHI"); to provide detailed information about a surgical simulation device, quality assurance phantom, or the like; to provide spatial orientation and registration information; or so on.

12 Claims, 7 Drawing Sheets

(51) Int. Cl.
  *A61B 90/96*  (2016.01)
  *G01R 33/58*  (2006.01)
  *A61B 90/90*  (2016.01)
  *A61B 90/94*  (2016.01)

(52) U.S. Cl.
  CPC .............. *A61B 90/90* (2016.02); *A61B 90/94* (2016.02); *A61B 2090/3933* (2016.02); *A61B 2090/3954* (2016.02); *A61B 2562/08* (2013.01)

(56) References Cited

U.S. PATENT DOCUMENTS

| | | |
|---|---|---|
| 2009/0177077 A1 | 7/2009 | Piferi et al. |
| 2011/0076983 A1 | 3/2011 | Rofougaran |
| 2012/0302863 A1 | 11/2012 | O'Neill |
| 2013/0053680 A1* | 2/2013 | Frey .................. A61B 6/12 |
| | | 382/128 |
| 2014/0070012 A1 | 3/2014 | Hunt et al. |
| 2014/0376336 A1* | 12/2014 | Steckner .............. G01R 33/288 |
| | | 367/197 |
| 2015/0223907 A1* | 8/2015 | Kieser .................... A61B 90/39 |
| | | 623/17.16 |

OTHER PUBLICATIONS

PCT International Preliminary Report on Patentability, PCT/IB2015/053396, dated Nov. 18, 2016.

* cited by examiner

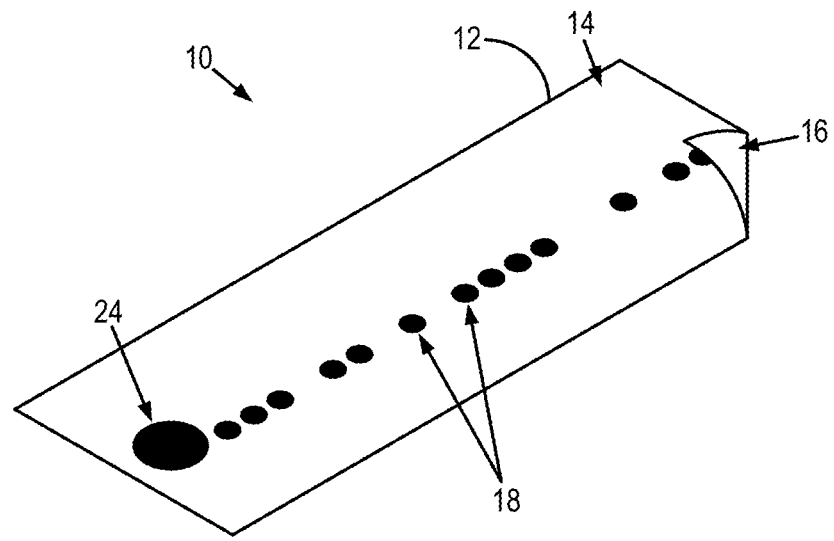
FIG. 1
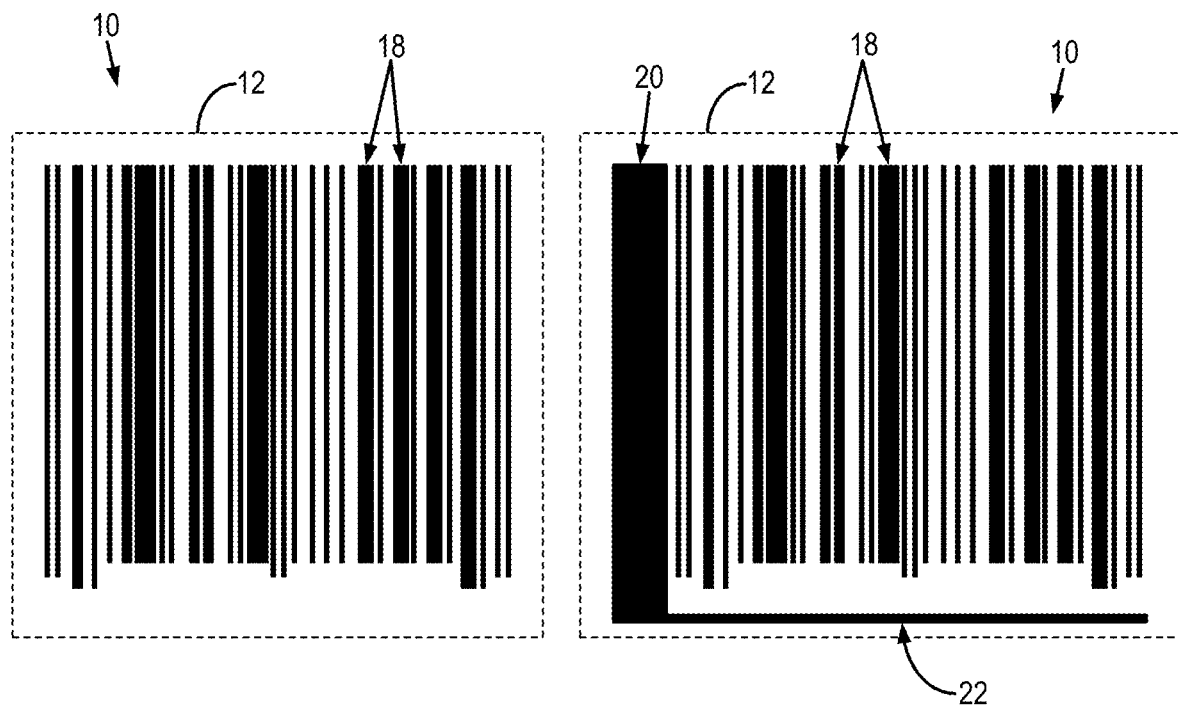
FIG. 2A
FIG. 2B

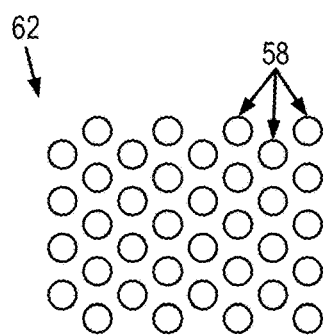
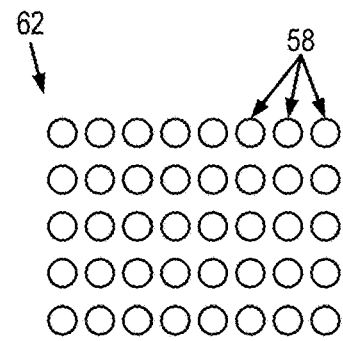
FIG. 12A  FIG. 12B
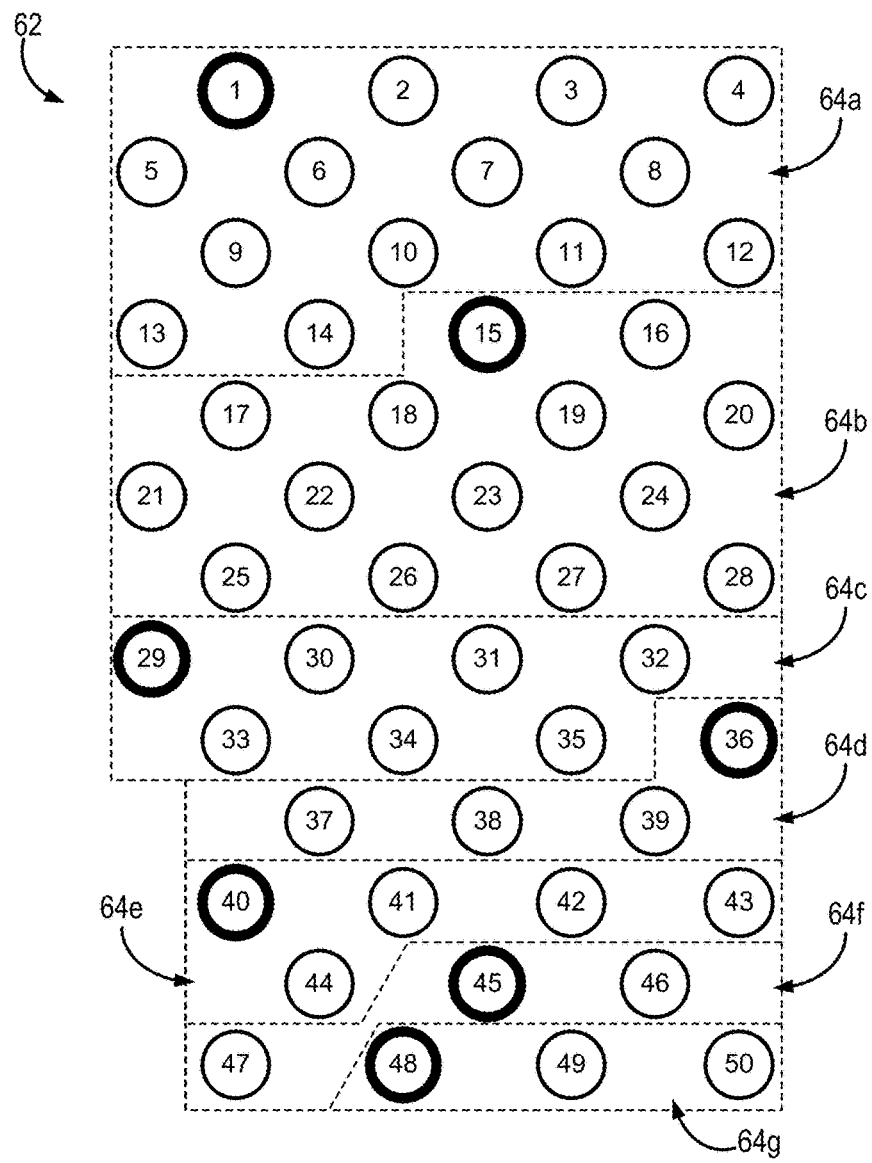
FIG. 13

MAGNETIC RESONANCE VISIBLE ASSEMBLY FOR ENCODING INFORMATION

CROSS-REFERENCE TO RELATED APPLICATIONS

This application is a continuation-in-part, and claims the benefit, of International Patent Application No. PCT/IB2015/053396, filed on May 8, 2015, and entitled "Magnetic Resonance Visible Labels and Markers for Encoding Information."

BACKGROUND OF THE DISCLOSURE

The field of the invention is systems and methods for magnetic resonance imaging ("MRI"). More particularly, the invention relates to systems and methods for labeling.

Typical MRI scanning procedures rely on the MRI system operator to input unique identifying characteristics of the subject or object being scanned. This information is then normally encoded into header information of the digital images generated by the scan. In various scenarios, however, this information may not be input, may be input incorrectly, or may need to be subsequently anonymized. Additionally, this identifying information only stays associated with the images as long the images remain in an image format that allows such header information to be associated with the image data, such as with DICOM-format images. If the images are converted to another format, the pertinent information may be lost.

There remains a desire to provide a form of subject or object labeling that does not rely on image header information. For example, when scanning phantom objects (e.g., for quality control purposes, scanner characterization purposes, patient simulations), there is rarely a rigorous identification process analogous to a medical record number for patients. Furthermore, there may be multiple phantoms that all give similar image characteristics and therefore cannot be simply differentiated by their image characteristics. Having some standardized method to identify the object as a phantom, and which phantom in particular, could be beneficial for automated post-processing evaluations or other image quality analysis methods.

Similarly, it would be desirable to have a method of uniquely identifying human subject scans, in addition to personal medical record numbers tagged in the digital header information, which would help resolve issues when patient information is input incorrectly. Such a method would also preferably provide an anonymized reference code compatible with image anonymization procedures.

SUMMARY OF THE DISCLOSURE

The present disclosure addresses the aforementioned drawbacks by providing a magnetic resonance visible assembly for encoding information. The assembly includes a substrate and a plurality of pins. The substrate has a first side and a second side, and a plurality of slots are formed in the substrate. The pins are arranged in the plurality of slots in the substrate. Each pins is composed of a material having magnetic resonance properties that are different from the magnetic resonance properties of the substrate, such that the plurality of pins are capable of being imaged with a magnetic resonance imaging ("MRI") system. The pins are arranged in the slots so as to generate a pattern that encodes information about an object being imaged with the MRI system.

It is an aspect of the present disclosure that the slots can be arranged in the substrate in an array. As one example, the slots can be arranged in the array based on a square packing arrangement. As another example, the slots can be arranged in the array based on a hexagonal packing arrangement. The slots can be indexed to define a plurality of segments that each encode a different piece of information. As one example, each of the plurality of segments can include a number of slots that are spatially adjacent each other. The pattern that encodes information about the object can include arranging pins in the array, or in each of the plurality of segments, to represent a binary encoding for each of the different pieces of information. The array can be symmetrical or asymmetrical.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 1 is an example of a magnetic resonance ("MR")-visible label having formed thereon a plurality of indicia that encode information about an object or subject being imaged, wherein the indicia are arranged to encode the information using a binary encoding;

FIG. 2A is an example of an MR-visible label in which the plurality of indicia are formed as a barcode;

FIG. 2B is an example of an MR-visible label in which the plurality of indicia are formed as a barcode having additional indicia that provide spatial orientation information about the label;

FIG. 12A is an example of an array of slots in an MR-visible assembly, in which the array has a hexagonal packing arrangement.

FIG. 12B is an example of an array of slots in an MR-visible assembly, in which the array has a square packing arrangement.

FIG. 13 is an example of an array of slots in an MR-visible assembly, in which the array includes a plurality of different segments of indexed slots such that each segment encodes a different piece of information.

DETAILED DESCRIPTION

Figure 3:
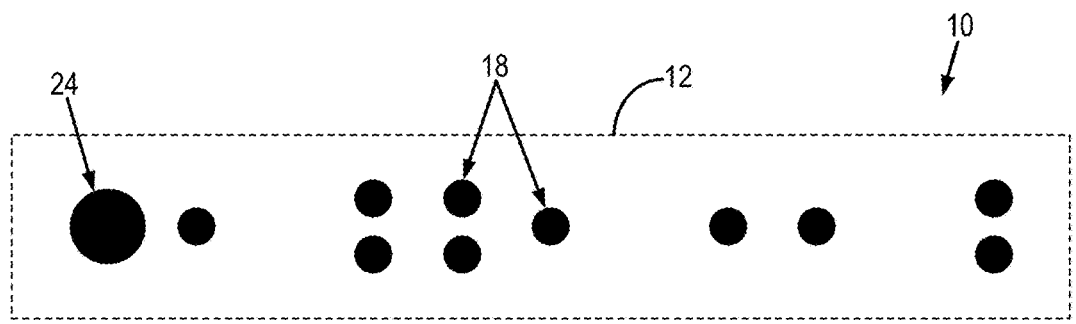
FIG. 3 is an example of an MR-visible label in which the plurality of indicia are arranged to encode information using a tertiary encoding.

Described here are systems and methods for manufacturing and using magnetic resonance ("MR") visible markers to encode information unique to the subject or object being imaged by an MRI system. As an example, the MR-visible markers can include MR-visible labels or MR-visible three-dimensional objects, such as an MR-visible assembly including a substrate having slots formed therein, into which MR-visible pins can be arranged in a pattern that encodes information. The use of such MR-visible markers enables unique identification of the imaged object by simple identification and processing of the MR images in which the marker is visible. By way of example, the object can be a subject or a phantom, such as a quality control or quality assurance phantom.

Generally speaking, the MR-visible markers described here can include any suitably designed MR-visible object that has a unique characteristic that allows it to be identified within typical MR images and that can encode information in numerous unique values. The MR-visible markers are preferably designed with spatially unique borders that allow for proper identification of the orientation of the MR-visible marker in a given MR image because any given MR image could represent the MR-visible marker with any arbitrary rotation or flip.

As mentioned above, in some embodiments the MR-visible markers of the present invention can include MR-visible labels, such as the label 10 illustrated in FIG. 1. As will be described below, in some other embodiments the MR-visible markers can include three-dimensional MR-visible objects.

In general, MR-visible labels 10 can include a substrate 12 having a first side 14 and a second side 16. The substrate 12 generally includes a sheet, and may be composed of a plastic, paper, or other similar material. The first side 14 of the substrate 12 includes a plurality of indicia 18 that are arranged into a pattern that encodes information about an object or subject to be imaged with an MRI system. A number of different examples of how these indicia 18 can be arranged is provided below, as are examples of the types of information that can be encoded in the pattern formed by the indicia 18.

The indicia 18 generally include a surface area having magnetic resonance properties that are different from the magnetic resonance properties of the substrate 12. As one example, the indicia 18 can be composed of a material that has a different longitudinal relaxation time, $T_1$, from the substrate 12. As other examples, the magnetic resonance properties can also include transverse relaxation time, $T_2$; proton density, $\rho$; magnetic susceptibility, $\chi$; or other magnetic resonance properties that can be utilized as the basis for generating an image contrast in an MR image.

In some embodiments, the second side 16 of the substrate 12 can include an adhesive layer for adhering the label to the receiving surface of an object or subject. Where the label 10 includes an adhesive layer, the substrate 12 can be provided on a liner, such as a liner paper. In some configurations, the adhesive layer is configured such that the label 10 can be releasably adhered to an object or subject. In these instances, the adhesive layer can be made from an easily removable adhesive, including removable pressure-sensitive adhesives, rubber-based hot-melt adhesives, and so on.

In some embodiments, the MR-visible label 10 includes indicia 18 formed using MR-visible inks, gels, or other materials that are deposited or otherwise coupled to the first side 14 of the substrate 12. One example of another material that is MR-visible and can be used to form indicia 18 is toothpaste, which can be printed or otherwise deposited on the substrate 12.

In general, the choice of MR-visible material from which the indicia 18 will be formed will be influenced by the complexity of the pattern in which the indicia 18 will be, the relative signal generated by the MR-visible material, and the spatial resolution necessary to resolve the detail in the pattern of indicia 18. For instance, when using MR-visible inks, a sufficient thickness of ink should be used to generate enough signal for the pattern of indicia 18 to be reliably imaged.

Referring now to FIGS. 2A and 2B, as one example, the indicia 18 can be arranged in a pattern that includes a plurality of line segments that are separated in space to create a barcode label. In these configurations, the barcode label can implement a universal product code ("UPC") barcode symbology; however, other barcode symbologies could also be readily implemented. Such indicia 18 can be created by printing the desired pattern on the substrate 12 of the label 10 using MR-visible inks, gels, or other materials. In other examples, such indicia 18 can be created by arranging thin strips of MR-visible material into the desired pattern. In these examples, the MR-visible material can include a material containing proton signals with short longitudinal relaxation time and moderate-to-long transverse relaxation time properties. For instance, the MR-visible material could include small tubes containing water doped with MR-visible material, such as vitamin E, gadolinium, iron oxide particles, or so on.

As illustrated in FIG. 2B, the barcode pattern can be augmented with additional lines that provide unique spatial orientation information, such as the thick bar 20 on the left of the barcode and the thin bar 22 running underneath the barcode.

As another example, the indicia 18 can be arranged in a pattern that includes a simple line of visible markers, such as those illustrated in FIG. 1. In these configurations, the indicia 18 can be arranged in a pattern that encodes information using a binary encoding. For example, the visible markers can be separated in space using a fixed spacing such that the presence or absence of a marker at a particular location can be respectively encoded as a binary value of "1" or "0." It will be appreciated that other encodings could be similarly implemented in this manner. As one example, illustrated in FIG. 3, a tertiary encoding could also be implemented. For a tertiary encoding, a linear pattern of zero, one, or two markers at fixed spacing can be used to encode values of "0," "1," or "2," respectively.

Referring again to FIG. 1, a linear pattern of indicia 18 can be augmented to include a visible, well-defined start location that not only indicates the beginning of the pattern, but provides unique spatial orientation information. As one example, such as the one illustrated in FIG. 1, this additional marker 24 can simply be a larger-sized marker; however, in other configurations the additional marker 24 could be uniquely shaped, or so on.

Figure 4:
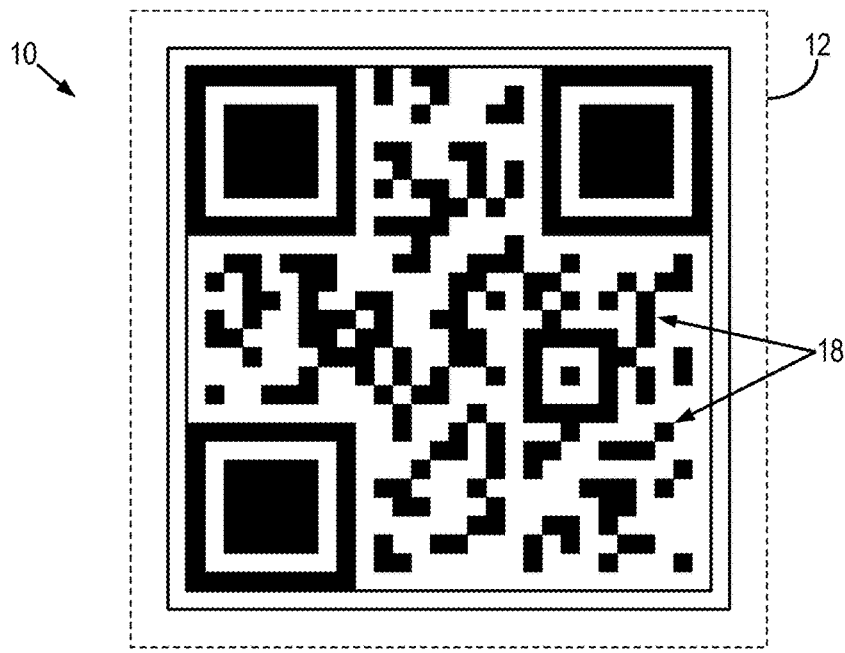
FIG. 4 is an example of an MR-visible label in which the plurality of indicia are formed as a quick response ("QR") code.

As another example, the indicia 18 can be arranged in a two-dimensional pattern that uniquely encodes information. For instance, the indicia 18 could be arranged as a quick response ("QR") code, as illustrated in FIG. 4. Such pattern of indicia 18 could be created by printing the desired pattern on the substrate 12 of the label 10 using MR-visible inks, gels, or other materials. Using two-dimensional patterns of indicia 18 has the benefit that more complex information can be encoded in a smaller label 10. Robust spatial orientation information can also be encoded in a QR code. As will be described below, this spatial orientation information can be used not only to identify the orientation of the subject within the field-of-view, but also to allow robust co-registration of images in which the label 10 is present. In some embodiments, the label 10 can serve as a target for co-registration, such that the pattern of indicia 18 aids in the co-registration process, such as through proper alignment of the pattern of indicia 18 in multiple different images.

Figure 5:
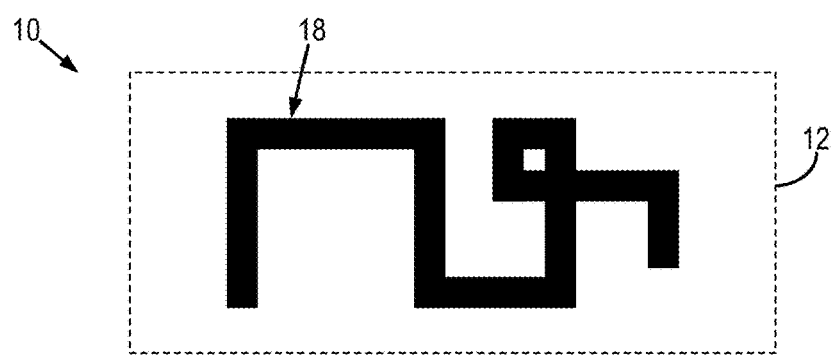
FIG. 5 is an example of an MR-visible label in which the plurality of indicia are formed as a unique two-dimensional geometric shape that, in this example, is arranged as a plurality of line segments.

In other configurations, the indicia 18 could be arranged as a one-dimensional or two-dimensional geometric pattern that is designed to be unique. One example of such a configuration is illustrated in FIG. 5, whereby a plurality of line segments are ordered to form a unique two-dimensional geometric pattern, or symbol, that can be used to encode information. In such configurations, the line segments can have a fixed length or a variable length.

In these foregoing examples, the indicia 18 can be created by printing the desired pattern on the substrate 12 of the label 10 using MR-visible inks, gels, or other materials. In other examples, the indicia 18 can include MR-visible beads or other markers that are coupled to the first side 14 of the substrate 12. As one example, the beads or other markers could include vitamin E tablets.

Figure 6:
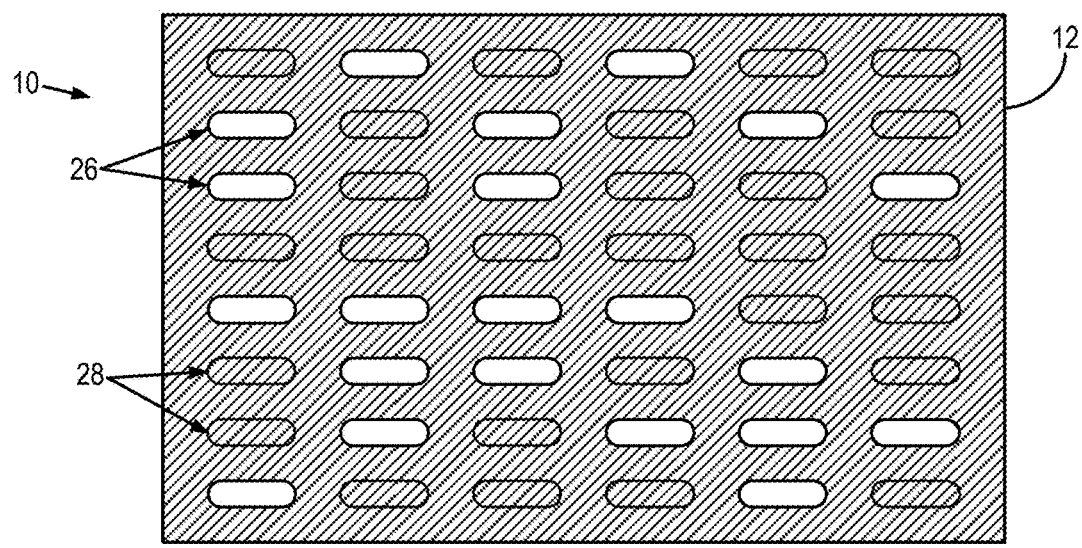
FIG. 6 is an example of an MR-visible label in which the plurality of indicia are formed as holes left when removing perforated regions of the label.

In some other embodiments, however, the indicia 18 can be formed by removing material from the substrate 12. As one example, the substrate 12 can be composed of an MR-visible material and can be manufactured to allow the simple removal of regions 26 from the substrate 12. For instance, regions 26 in the substrate 12 could be manufactured as perforated regions 28 that can be manually removed, or removed by the aid of an automated tool that punches out a pattern of these perforated regions 28 to form a pattern of indicia 18 in the substrate 12. An example of such a "punch-card" type of label 10 is illustrated in FIG. 6, wherein the indicia 18 can be formed by removing perforated regions 28 from the substrate 12.

As another example of indicia 18 that can be formed by removing material from the substrate 12, the substrate 12 can be composed of foil-backed paper. In this example, indicia 18 can be formed in the substrate 12 by cutting a pattern in the foil-backed paper. As one example, the foil-backed paper can be laser cut. As another example, the foil-backed paper can be cut using a machine, such as a printing press that has insertable die blocks. In this manner, the die blocks can be used to cut out shapes in a piece of foil-backed paper. A challenge with constructing the label 10 from foil-backed paper, however, is that the susceptibility artifacts generated by the foil may mean that the signal generating portions of the label could be partially obscured.

As mentioned above, in some embodiments, the MR-visible markers of the present invention can include three-dimensional MR-visible objects that are manufactured to contain a plurality of indicia that form a pattern that encodes information. In some embodiments, the plurality of indicia can be formed as a plurality of joined lined segments or shapes that together create a single geometric shape.

Three-dimensional MR-visible markers have the added benefit that they can be imaged in different imaging planes without moving the marker, thereby allowing images to be acquired in different orientations while still providing a marker that encodes information and is visible in the image. Markers can be arranged such that the same information is encoded when viewing the marker from different directions or, alternatively, such that different information is encoded when viewing the marker from different directions. As one example of the latter instances, different information can be encoded when viewing the marker in the axial plane, the coronal plane, or the sagittal plane. This differential encoding of information can be used, for example, to readily identify the plane through which the subject or object has been imaged.

Figure 7A:
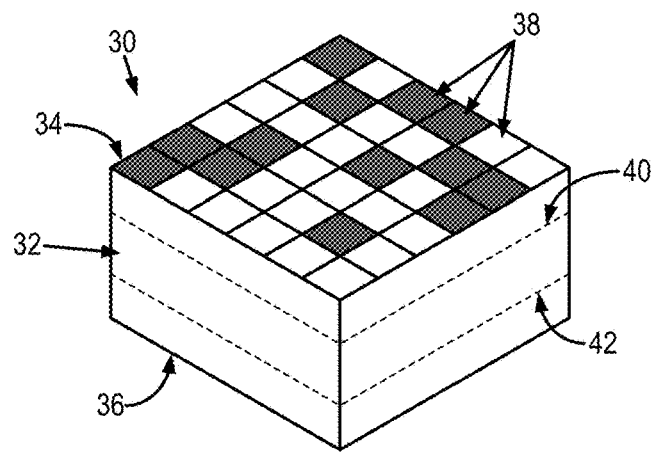
FIG. 7A is an example of a three-dimensional MR-visible marker having formed thereon a plurality of indicia that encode information about an object or subject being imaged.

One example of a three-dimensional MR-visible marker is illustrated in FIG. 7A. In general, such markers 30 can include a substrate 32 that extends from a first side 34 of the marker 30 to a second side 36 of the marker 30. A plurality of indicia 38 are then formed in the marker 30 such that the indicia 38 can be imaged using MRI and are arranged in a pattern or other manner such that information can be encoded by the indicia 38.

In some embodiments, the indicia 38 can include channels, wells, apertures, and so on that are formed in the substrate 32 and then filled with an MR-visible material. As one example, such indicia 38 can be filled with an MR-visible fluid, such as water doped with gadolinium, vitamin E, iron oxide particles, or another MR-visible material. In some other embodiments, the indicia 38 formed as channels, wells, apertures, and so on, can be left empty and the substrate 32 can be composed of an MR-visible material. In this manner, the substrate 32 will be visible in magnetic resonance images and the absence of signal caused by the indicia 38 will depict a pattern that can encode the desired information. It will be appreciated by those skilled in the art that the desired information can also be suitably encoded by the pattern associated with the depiction of the substrate 32 in the MR image. It will also be appreciated, then, that in some embodiments both the substrate 32 and the indicia 38 can be configured to form first and second patterns that both encode information.

Figure 7B:
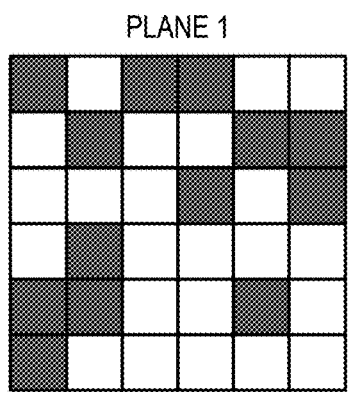
FIG. 7B is an example of an axial plane through the MR-visible marker of FIG. 7A illustrating a first pattern of indicia in the marker.
Figure 7C:
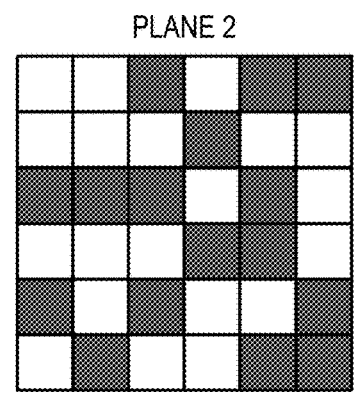
FIG. 7C is an example of another axial plane through the MR-visible marker of FIG. 7A illustrating a second pattern of indicia in the marker.
Figure 8:
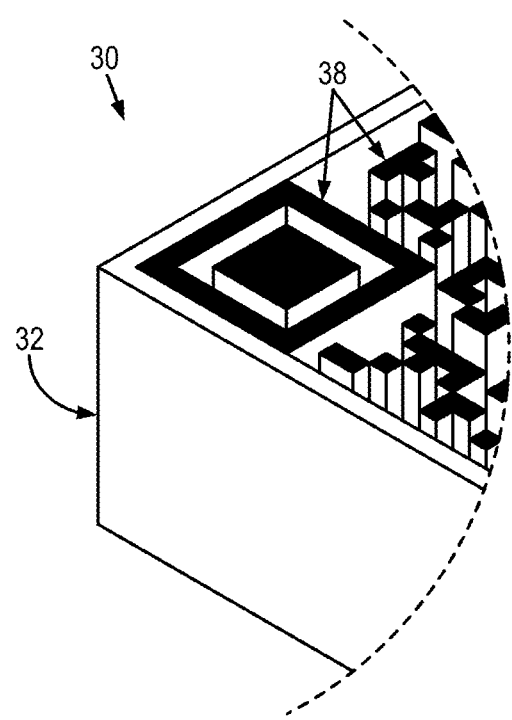
FIG. 8 is an example of a three-dimensional MR-visible marker in which the plurality of indicia are formed as a QR code when the marker is viewed through an axial plane.

The indicia 38 described above can be arranged such that the same pattern exists throughout the marker 30. Alternatively, as illustrated in FIGS. 7B and 7C, the indicia 38 can be arranged throughout the marker 30 such that different patterns are formed in different planes through the marker 30. For example, the pattern formed by the indicia 38 in a first plane 40 and be different from the pattern formed by the indicia 38 in a different, second plane. This configuration can be useful to encode different information in different image slices through the same subject or object. As one example, phantoms may have different properties or characteristics at different regions within the phantom. When imaging such a phantom, it can be useful to have information pertaining to these different regions encoded in the images of those regions. Using a suitably designed three-dimensional MR-visible marker, such differential information can be encoded across different slices in the imaging volume. When imaging a phantom that has different properties at different locations throughout the phantom, it can be useful to encode different information pertaining to those regions Like the MR-visible labels, the pattern of indicia 38 in the three-dimensional MV-visible markers 30 can be formed to encode information through numeric encoding (e.g., binary, tertiary), three-dimensional barcodes, three-dimensional QR codes, and so on. One example of a three-dimensional MR-visible marker 30 whose cross-section forms a QR-code is illustrated in FIG. 8.

Figures 9A, 9B:
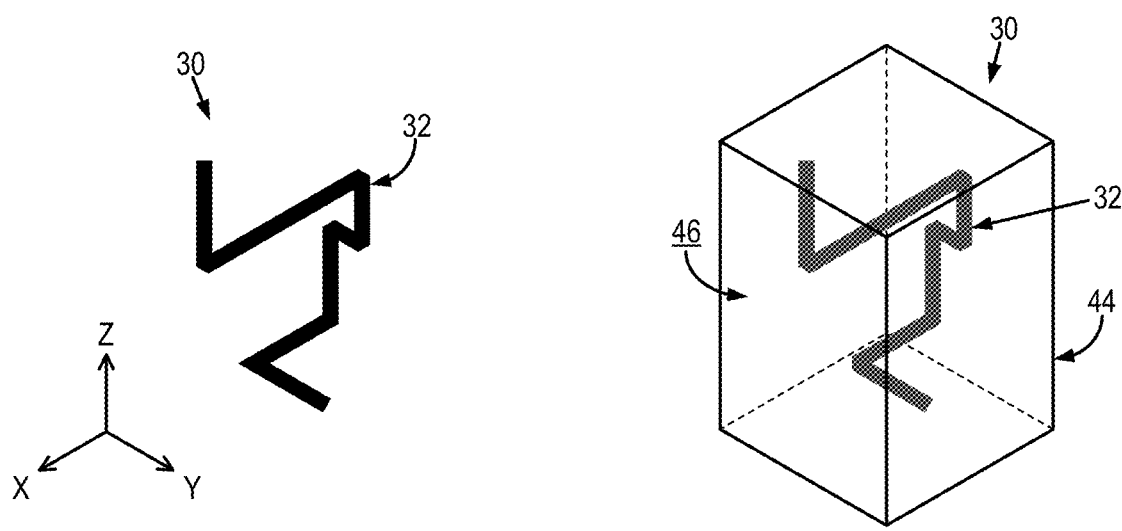
FIG. 9A is an example of a three-dimensional MR-visible marker formed as a unique three-dimensional shape that, in this example, is arranged as a plurality of linear segments.
FIG. 9B is an example of a three-dimensional MR-visible marker formed as a unique three-dimensional shape that is placed in a container that contains an MR-visible medium, such as an MR-visible fluid.

In other examples, the three-dimensional visible marker 30 can be constructed from a substrate 32 that is shaped in a unique, three-dimensional geometric shape, as illustrated in FIG. 9A. Such markers can be constructed using 3D printing or other suitable techniques. These markers can be composed of MR-visible materials such that they can be readily imaged using MRI. In some embodiments, markers 30 that are constructed as unique three-dimensional shapes can be made solid or hollow. For the latter configuration, the marker 30 can be filled with an MR-visible material or, alternatively, left empty while the marker 30 itself if formed from an MR-visible material.

As illustrated in FIG. 9B, in some other embodiments, the markers can be placed in a container 44 that contains an MR-visible medium 46, such as water doped with an MR-visible material. In these embodiments, the MR-visible marker 30 is composed of a material having magnetic resonance properties sufficiently different from the MR-visible medium 46, such that a sufficient image contrast exists between the marker 30 and the medium 46.

Figure 10:
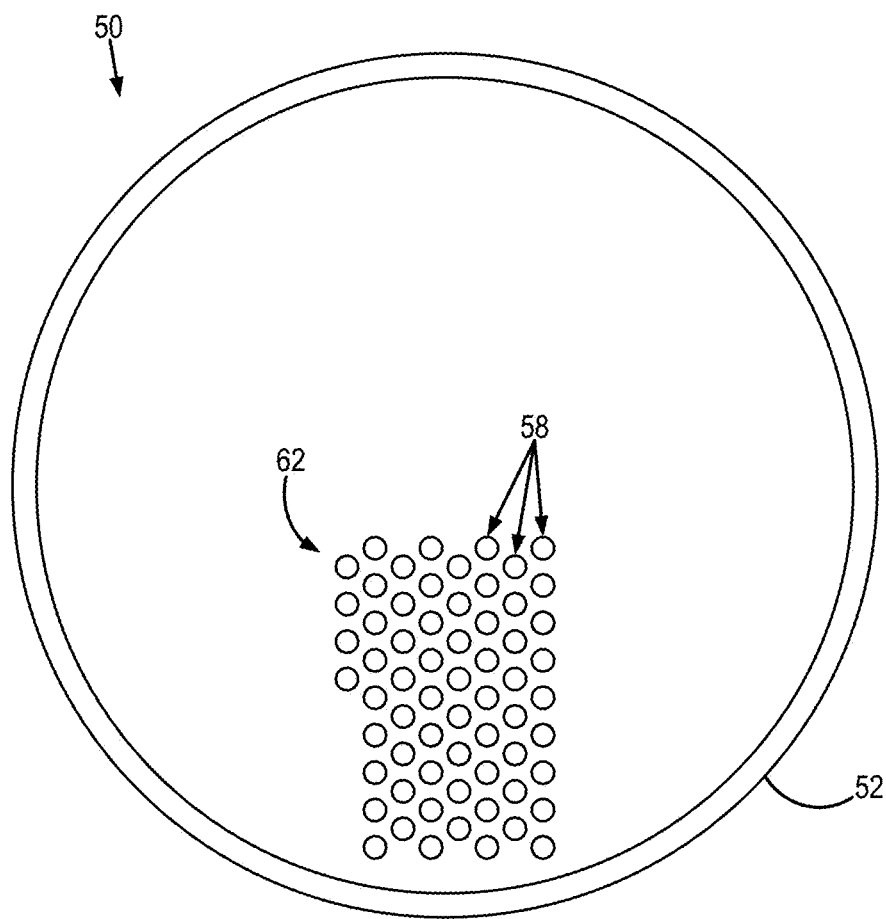
FIG. 10 is an example of an MR-visible assembly including slots formed in a substrate and MR-visible pins arranged in the slots to form a pattern that encodes information about an object or subject being imaged with an MRI system.

In other embodiments of the present disclosure, an MR-visible assembly for encoding information is provided. In FIG. 10, an example of such an MR-visible assembly 50 is shown. The MR-visible assembly 50 can form a part of an imaging phantom, a quality assurance phantom, or other medical device, or can be a self-standing object that can be imaged.

The MR-visible assembly 50 generally includes a substrate 52 having a first surface 54 and a second surface 56. The substrate 52 generally includes a plate, and may be composed of a plastic or other similar material. In the examples described above, the substrate 52 can be a plate that forms a part of an imaging or quality assurance phantom (e.g., a base of the imaging or quality assurance phantom).

A plurality of slots 58 are formed in the substrate 52. The slots 58 generally extend from the first surface 54 to the second surface 56 of the substrate 52. In some configurations, the slots 58 extend fully through the substrate 52, and in other configurations the slots 58 extend only partially below the first surface 54 of the substrate 52.

Figure 11:
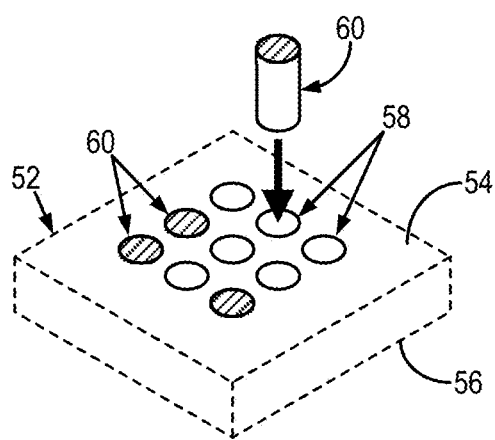
FIG. 11 is another view of an example MR-visible assembly including slots formed in a substrate and MR-visible pins arranged in the slots to form a pattern that encodes information about an object or subject being imaged with an MRI system.

Each slot 58 is sized and shaped to receive a pin 60, as shown in FIG. 11. The slots 58 can be circular in shape, such that the pins 60 will be cylindrical in shape, or other shapes can be used for the slots 58 (e.g., square, triangular, ellipsoidal) with the corresponding pins 60 having similarly shaped cross sections. The pins 60 can be secured in place in the slots 58, or can be removably positioned in the slots 58 to allow for adjustments to the information encoded by the MR-visible assembly 50.

The pins 60 are composed of a material with magnetic resonance properties that are different from the magnetic resonance properties of the substrate 52. As a result, the pins 60 are capable of being imaged with an MRI system such that they can be visually distinguished from the substrate 52 in a magnetic resonance image. As one example, the pins 60 can be composed of a material that has a different longitudinal relaxation time, $T_1$, from the substrate 52. As other examples, the magnetic resonance properties can also include transverse relaxation time, $T_2$; proton density, $\rho$; magnetic susceptibility, $\chi$; or other magnetic resonance properties that can be utilized as the basis for generating an image contrast in an MR image.

The slots 58 are generally arranged in the substrate 52 as an array to provide a compact design; however, other arrangements can also be implemented without detracting from the functionality of the MR-visible assembly 50. In one example, the slots 58 can be arranged in an array based on a hexagonal packaging arrangement, as illustrated in FIG. 12A. In another example, the slots 58 can be arranged in an array based on a square packing arrangement, as illustrated in FIG. 12B. It will be appreciated by those skilled in the art that other arrays can also be used.

The array of slots 58 can be generally symmetrical, as shown in FIGS. 11A and 11B, or can be asymmetrical, as shown in FIG. 10 (e.g., by having a different number of columns in certain rows, or a different number of rows in certain columns). Having an asymmetrical shape can facilitate determining the correct orientation of the MR-visible assembly 50 as viewed in an image of the assembly 50 such that the information encoded by the pattern of pins 60 in the slots 58 can be properly decoded. The correct orientation of the array of slots 58 can also be determined based on the orientation of the object being imaged or by one or more additional MR-visible markers that may be coupled to the substrate 52 (e.g., an MR-visible arrow that identifies the correct orientation of the array of slots 58, or that identifies the first index in the array of slots 58).

Pins 60 are arranged in the slots 58 to generate a pattern that is selected to encode information about the object being imaged with the MRI system. For example, the pins 60 can be arranged in the slots 58 to represent a binary encoding of information. For instance, a pin 60 can be coded as a "1" value and an empty hole 58 can be coded as a "0" value.

As shown in FIG. 13, the array 62 of slots 58 can be indexed to define a plurality of segments 64 that each encode a different piece of information. Slots 58 that are spatially adjacent one another are assigned incrementally larger index values. For example, index values can be assigned to the array 62 of slots 58 by starting in one corner of the array 62 and assigning incremental index values in any suitable manner (e.g., moving left-to-right in a row before moving down to the next row, as shown in FIG. 13; moving right-to-left in a row; moving top-to-bottom or bottom-to-top in a column before shifting a row; moving in a serpentine manner through rows or columns).

In the arrangement shown in FIG. 13, the slots 58 and pins 60 can encode the various pieces of information using a binary encoding. It will be appreciated by those skilled in the art, however, that other encoding schemes can also be used.

For example, using pins 60 with different magnetic resonance properties, other encoding schemes such as tertiary encoding can be implemented.

In the specific, non-limiting example shown in FIG. 13, seven different segments 64a-64g of slots 58 are shown. Each segment 64 encodes a different piece of information using an encoding scheme, such as a binary encoding scheme. Here, segment 64a contains fourteen slots 58, indexed with numbers 1-14; segment 64b contains fourteen slots 58, indexed with numbers 15-28; segment 64c contains seven slots 58, indexed with numbers 29-35; segment 64d contains four slots, indexed with numbers 36-39; segment 64e contains five slots 58, indexed with numbers 40-44; segments 64f contains three slots, indexed with numbers 45-47; and segment 64g contains three slots 58, indexed with numbers 48-50.

Each segment 64 includes an initial index that demarcates the beginning of the segment for purposes of encoding information. In the example shown in FIG. 13, the initial indices are slots 58 with index numbers 1, 15, 29, 36, 40, 45, and 48, as indicated by the bold outlining. When binary encoding is used, the segments 64 each individually encode a piece of information as a binary string. As one specific, non-limiting example, the array 62 illustrated in FIG. 13 can encode the following information,

TABLE 1

| | |
|---|---|
| Segment 64a: | 14-bit binary string encoding a SYN number identifying the type of object to which the MR-visible assembly 50 is coupled |
| Segment 64b: | 14-bit binary string encoding a serial number of the object to which the MR-visible assembly 50 is coupled |
| Segment 64c: | 7-bit binary string encoding a year of manufacture of the object to which the MR-visible assembly 50 is coupled |
| Segment 64d: | 4-bit binary string encoding a month of manufacture of the object to which the MR-visible assembly 50 is coupled |
| Segment 64e: | 5-bit binary string encoding a day of manufacture of the object to which the MR-visible assembly 50 is coupled |
| Segment 64f: | 3-bit binary string encoding a cyclical redundancy check ("CRC") code |
| Segment 64g: | Not in use |

It will be appreciated by those skilled in the art that other information can also be suitably encoded in the MR-visible assembly 50. For example, other numerical data can be encoded, including lot numbers, part numbers, and so on. Also, using binary or other encoding schemes, alphanumeric strings can be encoded. Other information, such as the material used to manufacture a device, materials used in the construction of an imaging or quality assurance phantom, and so on, can be associated with unique numeric or alphanumeric identifiers that can be encoded in the MR-visible assembly 50. Similarly, alphanumeric strings can be used to encode full words and so on.

Figure 14:
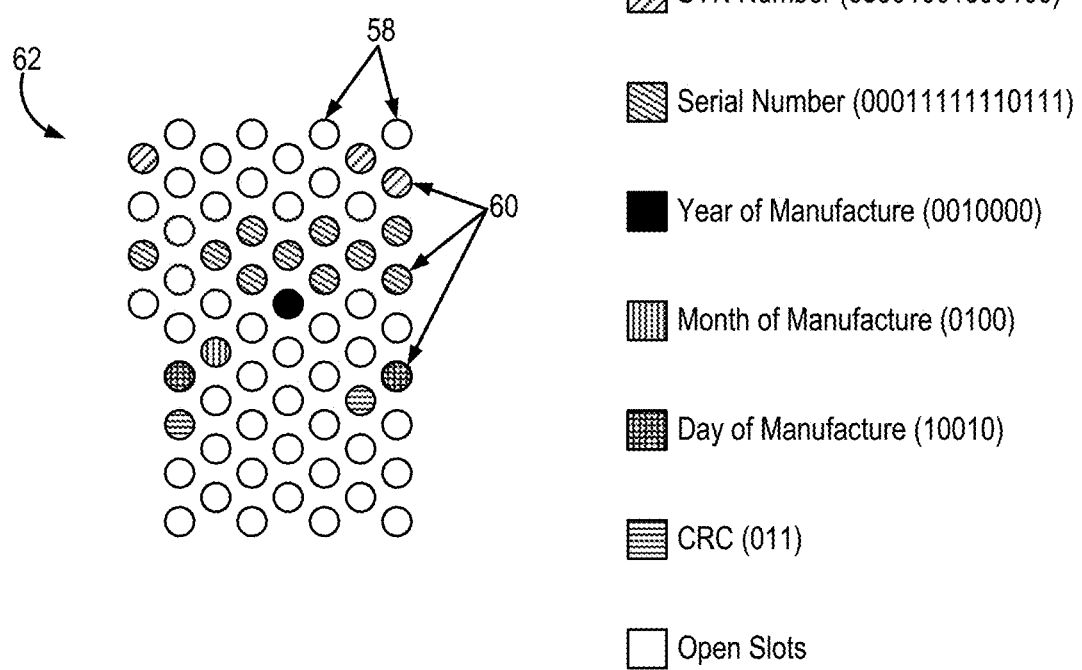
FIG. 14 is an example of an array of slots in an MR-visible assembly having pins arranged therein to form a pattern that encodes information about an object to be imaged with an MRI system as binary strings.

FIG. 14 illustrates an example pattern of pins 60 placed in the array 62 of slots 58 shown in FIG. 13. In this example, the pattern of pins 60 encodes a SYN number of 0580 (binary string 00001001000100), a serial number of 2039 (binary string 00011111110111), a date of manufacture of Apr. 18, 2016 (binary string 0010000 for a manufacture year of 16, binary string 0100 for a manufacture month of 04, binary string 10010 for a manufacture day of 18), and a CRC of 3 (binary string 011).

The CRC provides an error-detecting code. As one example, the CRC can be generated using a divisor polynomial. For instance, a diffusion imaging phantom can be coded with an SYN number of 0580 (binary string 00001001000100), a serial number of 1 (binary string 00000000000001), a year of manufacture of 16 (binary string, 0010000), a month of manufacture of 04 (binary string, 0100), and a day of manufacture of 12 (binary string 01100). The resulting code without the CRC is thus a 44-bit binary string of 00001001000100000000000000010010000010001100, which is the concatenation of the various binary strings noted above. Using a binary polynomial of 1011 ($X^3+X+1$) as the divisor, the CRC for this code would be 101. This CRC can encoded in the MR-visible assembly 50 as noted above, and appended to the 44-bit binary string associated with the particular diffusion imaging phantom.

Having described a number of different examples of MR-visible labels markers, and assemblies, a discussion of the different types of information that can be encoded in such labels, markers, and assemblies is now provided.

The amount of information that can be encoded in a given MR-visible label, marker, or assembly will depend on the pattern of indicia 18 or pins 60 used. For example, a barcode may be capable of encoding only twenty digits, whereas a QR code may be capable of encoding several thousand characters.

As such, patterns of indicia 18 or pins 60 that can encode fewer bits or characters are preferably used to encode smaller pieces of information that can then be related to more information that is stored in a separate storage device. For example, a barcode could be used to encode a unique identifier that is associated with an offline data storage containing a cache of information that may include protected health information, information otherwise stored in a DICOM header, and so on. Similarly, a barcode could be used to encode a part number for a phantom, implanted medical device, or so on.

Patterns of indicia 18 or pins 60 that are capable of encoding larger amount of information can similarly encode a unique identifier that is linked to a separate data storage, or can be used to encode a limited set of information about the subject or object being imaged. For example, a QR code may be capable of storing sufficient protected health information or, in the instance of an imaging phantom, may be capable of storing sufficient information about the phantom.

Examples of information about a phantom that can be encoded in an MR-visible label, marker, or assembly include part numbers, a description of the phantom type, the type of material(s) used in the phantom, manufacture dates, expiration dates, and so on. When a phantom is used for quality assurance or control, it may be important to know that the phantom has not degraded to a point where it is no longer reliable for quality assurance or control purposes. In this manner, it can be useful to encode manufacture dates, expiration dates, or both for phantoms that will degrade or otherwise change in a known way. Using this information, a phantom—or parts thereof—can be flagged as no longer being reliable when they have passed the encoded expiration date. In some embodiments, the materials used in the construction of the MR-visible label, marker, or assembly can degrade in a known way, such that the degradation of the label, marker, or assembly can be associated with the degradation or expiration of the phantom.

Other examples of information about a phantom that can be encoded include unique marker (s) that indicate the images contain phantom data, such that automated post-processing methods can interpret the unique marker to process or identify the images in a particular manner. The encoded information could also differentiate the source of the data (e.g., the exact phantom that was imaged) from phantom image sets that otherwise have an identical—or very similar—image appearance.

Advantageously, the MR-visible labels, markers, and assemblies described here can be used to encode unique identifiers for subjects being imaged in a clinical, or other, setting. As a result, confidential protected health information (e.g., medical record number, date of birth) does not need to be present in the image. By removing this personal information from the medical images, an additional level of security can be provided, further protecting sensitive protected health information.

The MR-visible labels, markers, or assemblies described here could also be constructed as a part of, inserted into, or otherwise coupled to, a simulation device or phantom, such as a poly(vinyl alcohol) (PVA) brain simulator/diffusion phantom. By using PVA formulations of varying density and an array of square or hexagonal wells with narrow walls that could be filled according to a desired QR code or geometric pattern, a unique $T_1$-visible or $T_2$-visible image set could be obtained for a given simulator or phantom. PVA formulations can also be doped with MR visible agents such as micro and sub-microsized particles containing iron or copper to modulate the MR signal. Stable polymeric dispersions in the PVA formulation could also be used with as precursor to a PVA hydrogel using a polymeric component containing an MR visible agent such as Vitamin E.

In some embodiments, the MR-visible label, marker, or assembly can be incorporated into a phantom or medical device itself. For instance, the substrate 12 can be formed in the phantom (or other medical device) and the plurality of indicia 18 formed, such as by an etching in the substrate 12. Similarly, the substrate 52 can be formed in the phantom (or other medical device) and the slots 58 machined therein, such as by drilling the slots 58 in the substrate 52.

As mentioned above, in addition to encoding pertinent information, the MR-visible labels, markers, or assemblies can also be used for identifying spatial points of reference in an image or for image registration and segmentation purposes. For example, an MR-visible label, marker, or assembly that contains spatial localization information, spatial orientation information, or both, can be coupled to a subject or object being imaged, such that the depiction of the MR-visible label, marker, or assembly, in the acquired images can be used to facilitate registration, segmentation, or other processing of the images. In some instances, the MR-visible label, marker, or assembly can be directly affixed to the subject being imaged.

In some instances, such as where MRI is used for surgical planning or radiation treatment planning, the MR-visible label, marker, or assembly can be coupled to a patient fixation device, thereby establishing a known position on the patient fixation device. The MR-visible label, marker, or assembly can then be used to positively establish the patient's location within the MRI system. If there is a previously established registration between the fixation device and previous images of the subject, the associated registration could be used to automatically direct the MRI system to image the subject at an already-segmented area of interest.

In some embodiments, the MR-visible label, marker, or assembly includes indicia 18 or pins 60 formed using a material that can be preferentially imaged using a delta relaxation enhanced magnetic resonance ("DREMR") acquisition. In general, a DREMR acquisition includes field-cycled relaxometry, or field-cycled imaging. The DREMR acquisition is an MRI technique that relies on using underlying tissue contrast mechanisms that vary with the strength of the applied magnetic field in order to generate unique image contrasts. To achieve DREMR contrast, the main magnetic field is varied as a function of time during specific portions of a pulse sequence. As one example, a field-shifting electromagnet coil can be used to perform this field variation.

The DREMR method exploits the difference in the $T_1$ dispersion property (i.e., the variation of $T_1$ with field strength) of targeted $T_1$ contrast agents in bound and unbound states. In particular, this difference is exploited to obtain an image that contains signal only from the contrast agent that is in the bound state, while suppressing signal from the contrast agent in the unbound state.

One example of a contrast agent material that can be preferentially imaged using a DREMR acquisition is iron oxide. The $T_1$ relaxation time of iron oxide based contrast agents vary with the strength of the magnetic field. Therefore, the DREMR method can be used in order to obtain images that contain signal specifically where iron oxide-based contrast agents have accumulated.

The present disclosure has described one or more preferred embodiments, and it should be appreciated that many equivalents, alternatives, variations, and modifications, aside from those expressly stated, are possible and within the scope of the invention.

The invention claimed is:

1. A magnetic resonance visible assembly for encoding information, comprising:
   a substrate having a first side and a second side, and wherein a plurality of slots are formed in the substrate;
   a plurality of pins arranged in the plurality of slots in the substrate, each of the plurality of pins being composed of a material having magnetic resonance properties that are different from magnetic resonance properties of the substrate such that the plurality of pins are capable of being imaged with a magnetic resonance imaging (MRI) system;
   wherein the plurality of pins are arranged in the plurality of slots so as to generate a pattern such that the pattern encodes information about an object being imaged with the MRI system;
   wherein the plurality of pins are removably arranged in the plurality of slots, thereby allowing for adjustments to the encoded information about the object being imaged with the MRI system; and
   wherein the substrate is a plate that forms a part of a phantom.

2. The magnetic resonance visible assembly of claim 1, wherein the plurality of slots are arranged in the substrate in an array.

3. The magnetic resonance visible assembly of claim 2, wherein the slots are arranged in the array based on a square packing arrangement.

4. The magnetic resonance visible assembly of claim 2, wherein the slots are arranged in the array based on a hexagonal packing arrangement.

5. The magnetic resonance visible assembly of claim 2, wherein the slots are indexed to define a plurality of segments such that each of the plurality of segments encodes a different piece of information.

6. The magnetic resonance visible assembly of claim 5, wherein each of the plurality of segments includes a number of the plurality of slots that are spatially adjacent each other.

7. The magnetic resonance visible assembly of claim 6, wherein the pattern includes arranging pins in each of the plurality of segments to represent a binary encoding for each of the different pieces of information.

8. The magnetic resonance visible assembly of claim 5, wherein the different pieces of information include at least one of a serial number, a year of manufacture, a month of manufacture, or a day of manufacture.

9. The magnetic resonance visible assembly of claim 2, wherein the plurality of slots and the plurality of pins are arranged in the pattern to represent a binary encoding of information.

10. The magnetic resonance visible assembly of claim 2, wherein the array is an asymmetrical array.

11. The magnetic resonance visible assembly of claim 1, wherein the information encoded by the pattern includes at least one of a serial number of the phantom, a year of manufacture of the phantom, a month of manufacture of the phantom, a day of manufacture of the phantom, or information about materials used in the phantom.

12. The magnetic resonance visible assembly of claim 1, wherein the plurality of slots extend completely through the substrate from the first side to the second side.

* * * * *